(12) United States Patent
Sawamura et al.

(10) Patent No.: US 7,838,697 B2
(45) Date of Patent: Nov. 23, 2010

(54) MANUFACTURING METHOD OF ORGANOBORON COMPOUND

(75) Inventors: Masaya Sawamura, Sapporo (JP); Hajime Ito, Sapporo (JP)

(73) Assignee: Nippon Chemical Industrial Co., Ltd., Hokkaido (JP)

( * ) Notice: Subject to any disclaimer, the term of this patent is extended or adjusted under 35 U.S.C. 154(b) by 141 days.

(21) Appl. No.: 12/100,805

(22) Filed: Apr. 10, 2008

(65) Prior Publication Data

US 2008/0262257 A1 Oct. 23, 2008

(30) Foreign Application Priority Data

Apr. 13, 2007 (JP) ............................. 2007-106170

(51) Int. Cl.
*C07F 7/02* (2006.01)
(52) U.S. Cl. .......................................... 556/402; 568/1
(58) Field of Classification Search ....................... None
See application file for complete search history.

(56) References Cited

PUBLICATIONS

Ito et al, {Copper-Catalyzed -Selective and Stereospecific Substitution Reaction of Allylic Carbonates with Diboron: Efficient Route to Chiral Allylboron Compounds, Journal of the American Chemical Society (2005), 127(46), 16034-16035}.*

Kabalka et al., {Pd-Catalyzed Cross-Coupling of Baylis-Hillman Acetate Adducts with Bis(pinacolato)diboron: An Efficient Route to Functionalized Allyl Borates, Journal of Organic Chemistry (2004), 69(17), 5807-5809}.*

Ito et al., {Copper-Catalyzed Enantioselective Substitution of Allylic Carbonates with Diboron: An Efficient Route to Optically Active -Chiral Allylboronates, Journal of the American Chemical Society (2007), 129(48), 14856-14857}.*

Ditrich et al., "Total Synthesis of Mycinolide V, the Aglycone of a Macrolide Antibiotic of the Mycinamycin Series," Angewandte Chemie International Edition, vol. 25, No. 11, pp. 1028-1030, 1986.

Pelz et al., "Palladium-Catalyzed Enantioselective Diboration of Prochiral Allenes," Journal of the American Chemical Society, vol. 126, No. 50, pp. 16328-16329, 2004.

Ito et al., "Copper-Catalyzed γ-Selective and Stereospecific Substitution Reaction of Allylic Carbonates with Diboron: Efficient Route to Chiral Allylboron Comnpounds," Journal of the American Chemical Society, vol. 127, No. 46, pp. 16034-16035, 2005.

Charette et al., "Synthesis of Contiguous Cyclopropanes by Palladium-Catalyzed Suzuki-Type Cross-Coupling Reactions," Tetrahedron Letters, vol. 38, No. 16, 2809-2812, 1997.

Miller et al., "An Efficient and Highly Enantio- and Diastereoselective Cyclopropanation of Olefins Catalyzed by Schiff-Base Ruthenium(II) Complexes," Angewandte Chemie International Edition, vol. 41, No. 16, pp. 2953-2956, 2002.

Hildebrand et al., "A Novel, Stereocontrolled Synthesis of 1,2-*trans*-Cyclopropanes: Cyclopropyl Boronate Esters as Partners in Suzuki Couplings with Aryl Halides," Synlett, vol. 41, pp. 893-894, 1996.

Pietruzska et al., "Enantiomerically Pure Cyclopropylboronic Esters: Auxiliary- *versus* Substrate-control," Journal of the Chemical Society, Perkin Trans. 1, pp. 4293-4300, 2000.

Rubina et al., "Catalytic Enantioselective Hydroboration of Cyclopropenes," Journal of the American Chemical Society, vol. 125, No. 24, pp. 7198-7199, 2003.

* cited by examiner

*Primary Examiner*—Daniel M Sullivan
*Assistant Examiner*—Chukwuma O Nwaonicha
(74) *Attorney, Agent, or Firm*—Greenblum & Bernstein, P.L.C.

(57) ABSTRACT

A manufacturing method for one of, or a mixture of, an optically active allylboron compound and racemic or optically active boryl cyclopropane, including a coupling reaction, in the presence of a catalyst, between allyl compound and diboron compound. It is preferred that a copper (I) complex is used as the catalyst. It is preferred that a counterion of the copper (I) complex is an alkoxide or a hydride. It is preferred that the copper (I) complex has a phosphine ligand. It is preferred that the phosphine ligand is a chiral phosphine ligand.

15 Claims, No Drawings

MANUFACTURING METHOD OF ORGANOBORON COMPOUND

CROSS-REFERENCE TO RELATED APPLICATIONS

The present application claims priority under 35 U.S.C. §119 of Japanese Application No. 2007-106170, filed on Apr. 13, 2007, the disclosure of which is expressly incorporated by reference herein in its entirety.

BACKGROUND OF THE INVENTION

1. Field of the Invention

The present invention relates to a manufacturing method of an organoboron compound. An organoboron compound obtained by using the manufacturing method is widely used as a reactant in organic synthesis, such as a reaction in which the organoboron compound diastereoselectively reacts with a carbonyl compound to produce a homoallylic alcohol.

2. Description of Related Art

Since an allylboron compound diastereoselectively reacts with a carbonyl compound to produce a homoallylic alcohol, it is well known as a useful reactant in organic synthesis. For example, by reacting with an aldehyde, an anti-homoallylic alcohol can be obtained from an (E)-allylboron compound, and a syn-homoallylic alcohol can be synthesized from a (Z)-allylboron compound.

An optically active allylboron compound also can similarly selectively allylate a carbonyl compound under a moderate condition, and, along with a chiral transformation, produce an optically active homoallylic alcohol, and therefore, is a useful reactant. However, in an existing synthesis method, a super-stoichiometric amount of chiral auxiliary is required, and, in addition, a multi-step synthesis is required (Related Art 1). On the other hand, there is practically no example of synthesizing an optically active allylboron compound by using a catalytic chiral synthesis, except a relatively special example of diborylating an allene compound by using an optically active palladium catalyst (Related Art 2). The two examples are both difficult to be applied to the case of a compound having a complicated skeleton or the case of a functionalized compound.

Separately from the above-mentioned technologies, a selective synthesis method of synthesizing an allylboron compound from an allyl carbonate ester and a diboron has been developed that uses a copper (I) phosphine complex catalyst (Related Art 3). In this reaction, a boron substituent is selectively introduced at a γ-position with respect to an elimination group. In the case where an optically active allyl carbonate ester is used, along with a highly efficient chiral transformation, an optically active allylboron compound can be efficiently synthesized. This method is a useful method that enables selective synthesis of an allylboron compound having a functional group and a polysubstituted allylboron compound, which are so far difficult to synthesize. However, since an optically active allyl carbonate ester is required, there has been no report that an optically active allylboron compound has been synthesized from starting material having no optically active component.

Separately from an allylboron compound, a cyclopropane skeleton is a structure that is widely found in natural products, functional materials such as a liquid crystal, and organic compounds. In particular, natural products having cyclopropane rings, and their derivatives have attracted the interests of many Japanese and international scientists, with respect to their pharmacological activity, biosynthesis, and chiral synthesis. This is an area of active research even after over 120 years since William Henry Perkin first synthesized a cyclopropane derivative in 1884.

Since most of natural products having cyclopropane skeletons have multiple chiral points in cyclopropane rings, their chiral syntheses are particularly important. At the present, the most used cyclopropane synthesis method is a technique that utilizes metal carbenoid generation such as the Simmons-Smith reaction. In the past 20 years, chiral synthesis has been further developed, and a technique utilizing a chiral auxiliary (Related Art 4) and an enantioselective technique utilizing a transition metal catalyst (Related Art 5) have been developed.

These techniques utilize double bonds that exist in a molecule to construct a cyclopropane ring. With regard to this, a method has been developed in recent years that utilizes a coupling reaction to directly introduce a pre-synthesized cyclopropane skeleton into a molecule. When a boryl cyclopropane having a boron substituent on a cyclopropane is synthesized, and is applied to the Suzuki-Miyaura coupling reaction that is widely used in organic synthesis, a product is obtained that has a cyclopropane skeleton introduced therein. So far, there have been research reports from multiple research groups (Related Art 4 and Related Art 6).

Here, when an optically active boryl cyclopropane can further be synthesized, it is possible to introduce an optically active cyclopropane skeleton. However, in this case, the issue is a more efficient synthesis of the optically active boryl cyclopropane.

So far reported optically active boryl cyclopropane synthesis methods can be broadly categorized as the following two techniques. First, an example of techniques that have been studied since some time ago is the technique that pre-introduces a chiral auxiliary group on boron, and utilizes carbenoid generation to diastereoselectively construct a cyclopropane ring (Related Art 7). On the other hand, an enantioselective hydroboration reaction with respect to a disubstituted cyclopropane utilizing a chiral catalyst was recently reported (Related Art 8). The synthesis that utilizes a chiral auxiliary agent requires an equal or larger amount of chiral source with respect to a substrate, and its selectivity is not extremely high. On the other hand, although the catalytic chiral synthesis is a useful technique in that a target product can be obtained from a small amount of chiral source with a high enantioselectivity, this is the only report about an optically active boryl cyclopropane, and it has a limitation with respect to applicable scope of the substrate, such as that it is limited to a substrate activated by an ester substituent.

| [Related Art 1] | Angew. Chem. Int. Ed. 25 (1986) 1028-1030. |
| [Related Art 2] | J. Am. Chem. Soc. 126 (2004) 16328-16329. |
| [Related Art 3] | J. Am. Chem. Soc. 127 (2005) 16034-16035. |
| [Related Art 4] | Tetrahedron Lett. 38 (1997) 2809-2812. |
| [Related Art 5] | Angew. Chem. Int. Ed. 41 (2002) 2953-2956. |
| [Related Art 6] | Synlett. 41 (1996) 893-895. |
| [Related Art 7] | J. Chem. Soc., Perkin Trans. 1 (2000) 4293-4300. |
| [Related Art 8] | J. Am. Chem. Soc. 125 (2003) 7198-7199. |

SUMMARY OF THE INVENTION

Accordingly, a purpose of the present invention is to provide a manufacturing method of an organoboron compound that is useful as a reactant in an organic reaction.

As results of intensive studies directed to achieving the above-mentioned object, the inventors of the present invention found that an optically active allylboron compound or an optically active boryl cyclopropane compound, having high enantioselectivity, can be obtained by an action of a diboron compound on an allyl compound in the presence of a catalyst. The inventors further found that, not only in the case where an optically active catalyst is used, but also in the case where an optically inactive catalyst is used, a boryl cyclopropane compound can be obtained when a substance having a specific group such as substituted silyl group is used as an allyl compound.

More specifically, the present invention is to provide a manufacturing method of an organoboron compound as shown by below-listed general formula (3) or general formula (4), the manufacturing method including a coupling reaction, in the presence of a catalyst, between an allyl compound as shown by below-listed general formula (1) and a diboron compound as shown by below-listed general formula (2).

[General formula (1)]

(where R represents a hydrogen atom, an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an alkyloxy carbonyl group, an aralkyloxy carbonyl group, or a substituted silyl group; E is an elimination group, and represents a carbonate ester, a carboxylate ester, ether, a phosphate ester or a sulfonate ester; and the wavy line represents that either a trans- or a cis-isomer is possible.)

[General formula (2)]

(where X represents identical or different atoms each having an isolated electron pair; the dotted lines connecting adjacent Xs represent that other atoms are bound to Xs; and adjacent Xs may form a ring via other atoms.)

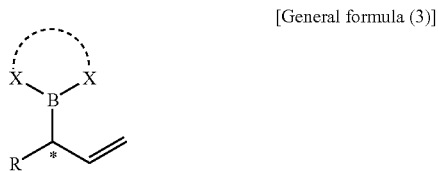

[General formula (3)]

(where R and X are the same as above described; and * represents a chiral carbon.)

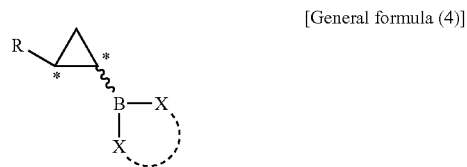

[General formula (4)]

(where R and X are the same as above described; * represents a chiral carbon; and the wavy line represents that either a trans- or a cis-isomer is possible.)

The manufacturing method of an organoboron compound of the present invention is a manufacturing process having a superior reaction catalyst activity and/or optical selectivity, and is therefore industrially highly useful. Further, an organoboron compound manufactured according to the present invention is important as an intermediate or final product of a medicine, an agricultural, chemical or a biologically active substance. For example, it is a highly useful compound as a synthetic intermediate of an antibiotic substance.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention.

An allyl compound that is a starting material in the present invention is as shown by general formula (1). In general formula (1), an alkyl group that is represented by R may be in a form of a straight-chain or a branch. Examples of the alkyl group include alkyl groups having a number of carbon atoms from 1 to 6. More specifically, the examples include a methyl group, an ethyl group, an n-propyl group, a 2-propyl group, an n-butyl group, a 2-butyl group, an isobutyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a tert-hexyl group, a 2-methylpentyl group, a 3-methylpentyl group, a 4-methylpentyl group, a 5-methylpentyl group, and the like.

Examples of an cycloalkyl group that is represented by R in general formula (1) include cycloalkyl groups having a number of carbon atoms from 3 to 7. More specifically, the examples include a cyclopropyl group, a cyclobutyl group, a cyclopentyl group, a cyclohexyl group, a cycloheptyl, a 2-methylcyclopentyl group, a 3-methylcyclopentyl group, a cycloheptyl group, a 2-methylcyclohexyl group, a 3-methylcyclohexyl group, a 4-methylcyclohexyl group and the like.

Examples of an aralkyl group that is represented by R in general formula (1) include aralkyl groups having a number of carbon atoms from 7 to 12. More specifically, the examples include a benzil group, a 2-phenylethyl group, a 1-phenylpropyl group, a 2-phenylpropyl group, a 3-phenylpropyl group, a 1-phenylbutyl group, a 2-phenylbutyl group, a 3-phenylbutyl group, a 4-phenylbutyl group, a 1-phenylpentyl group, a 2-phenylpentyl group, a 3-phenylpentyl group, a 4-phenylpentyl group, 5-phenylpentyl group, a 1-phenylhexyl group, a 2-phenylhexyl group, a 3-phenylhexyl group, a 4-phenylhexyl group, 5-phenylhexyl group, a 6-phenylhexyl group, and the like.

Examples of an aryl group that is represented by R in general formula (1) include aryl groups having a number of carbon atoms from 6 to 14. More specifically, the examples include a phenyl group, a naphthyl group and an anthryl group.

Examples of an aliphatic heterocyclic group that is represented by R in general formula (1) desirably include 5- or 6-membered aliphatic heterocyclic groups, and also include aliphatic heterocyclic groups containing from 1 to 3 heteroatoms such as a nitrogen atom, an oxygen atom and a sulfur atom. More specifically, the examples include a pyrrolidinyl-2-on group, a piperidino group, a piperazinyl group, a morpholino group, a tetrahydrofuryl group, a tetrahydropyranyl group, and the like.

Examples of an aromatic heterocyclic group that is represented by R in general formula (1) desirably include 5- or 6-membered monoaromatic and polyaromatic heterocyclic groups, and also include aromatic heterocyclic groups containing from 1 to 3 heteroatoms such as a nitrogen atom, an oxygen atom and a sulfur atom. More specifically, the examples include a pyridyl group, an imidazolyl group, a thiazolyl group, a furfuryl group, a pyranyl group, a furyl group, a benzofuryl group and a thienyl group.

An alkoxy group that is represented by R in general formula (1) may be in a form of a straight-chain, a branch, or a ring. Examples of the alkoxy group include alkoxy groups having a number of carbon atoms from 1 to 6. More specifically, the examples include a methoxy group, an ethoxy group, an n-propoxy group, a 2-propoxy group, an n-butoxy group, a 2-butoxy group, an isobutoxy group, a tert-butoxy group, an n-pentyloxy group, a 2-methylbutoxy group, a 3-methylbutoxy group, a 2,2-dimethylpropyloxy group, an n-hexyloxy group, a 2-methylpentyloxy group, a 3-methylpentyloxy group, a 4-methylpentyloxy group, a 5-methylpentyloxy group, a cyclohexyloxy group, and the like.

Examples of aralkyloxy group that is represented by R in general formula (1) include aralkyloxy groups having a number of carbon atoms from 7 to 12. More specifically, the examples include a benzyloxy group, a 2-phenylethoxy group, a 1-phenylpropoxy group, a 2-phenylpropoxy group, a 3-phenylpropoxy group, a 1-phenylbutoxy group, a 2-phenylbutoxy group, a 3-phenylbutoxy group, a 4-phenylbutoxy group, a 1-phenylpentyloxy group, a 2-phenylpentyloxy group, a 3-phenylpentyloxy group, a 4-phenylpentyloxy group, a 5-phenylpentyloxy group, a 1-phenylhexyloxy group, a 2-phenylhexyloxy group, , a 3-phenylhexyloxy group, a 4-phenylhexyloxy group, a 5-phenylhexyloxy group, a 6-phenylhexyloxy group, and the like.

Examples of aryloxy group that is represented by R in general formula (1) include aryloxy groups having a number of carbon atoms from 6 to 14. More specifically, the examples include a phenyloxy group, a naphthyloxy group, an anthryloxy group, and the like.

In general formula (1), an alkyloxy carbonyl group that is represented by R may be in a form of a straight-chain or a branch. Examples of the alkyloxy carbonyl group include alkyloxy carbonyl groups having a number of carbon atoms from 2 to 7. More specifically, the examples include a methoxy carbonyl group, an ethoxy carbonyl group, a propoxy carbonyl group, a butoxy carbonyl group, a tert-butoxy carbonyl group, a pentyloxy carbonyl group, a hexyloxy carbonyl group, a heptyloxy carbonyl group, and the like.

Examples of an aralkyloxy carbonyl group that is represented by R in general formula (1) include aralkyloxy carbonyl groups having a number of carbon atoms from 8 to 12. More specifically, the examples include a benzyloxy carbonyl group and a phenylethoxy carbonyl group.

Examples of a substituted alkyl group include alkyl groups formed by substituting at least one hydrogen atom of each of the above-mentioned alkyl groups with a substituent such as an alkyl group, a cycloalkyl group, an alkoxy group, a halogen atom, an amino group, or an amino group having a protective group.

Examples of a substituted cycloalkyl group include cycloalkyl groups formed by substituting at least one hydrogen atom of each of the above-mentioned cycloalkyl groups with a substituent such as an alkyl group, a cycloalkyl group, an alkoxy group, a halogen atom, an amino group, or an amino group having a protective group.

Examples of a substituted aralkyl group include aralkyl groups formed by substituting at least one hydrogen atom of each of the above-mentioned aralkyl groups with a substituent such as an alkyl group, a cycloalkyl group, an alkyl halide group, an alkoxy group, a halogen atom, an amino group, and an alkyl-substituted amino group.

Examples of a substituted aryl group include aryl groups formed by substituting at least one hydrogen atom of each of the above-mentioned aryl groups with a substituent such as an alkyl group, a cycloalkyl group, an alkyl halide group, an alkoxy group, a halogen atom, an amino group, and an alkyl-substituted amino group, and also include aryl groups formed by substituting two adjacent hydrogen atoms of each of the above-mentioned aryl groups with a substituent such as an alkylenedioxy group.

Examples of a substituted aliphatic heterocyclic group include aliphatic heterocyclic groups formed by substituting at least one hydrogen atom of each of the above-mentioned aliphatic heterocyclic groups with a substituent such as an alkyl group, a cycloalkyl group, an alkyl halide group, an alkoxy group, and a halogen atom.

Examples of a substituted aromatic heterocyclic group include aromatic heterocyclic groups formed by substituting at least one hydrogen atom of each of the above-mentioned aromatic heterocyclic groups with a substituent such as an alkyl group, a cycloalkyl group, an alkyl halide group, an alkoxy group, and a halogen atom.

Examples of a substituted alkoxy group include alkoxy groups formed by substituting at least one hydrogen atom of each of the above-mentioned alkoxy groups with a substituent such as an alkyl group, a cycloalkyl group, an alkoxy group, a halogen atom, an amino group, or an amino group having a protective group.

Examples of a substituted aralkyloxy group include aralkyloxy groups formed by substituting at least one hydrogen atom of each of the above-mentioned aralkyloxy groups with a substituent such as an alkyl group, a cycloalkyl group, an alkyl halide group, an alkoxy group, a halogen atom, an amino group, and an alkyl-substituted amino group.

Examples of a substituted aryloxy group include aryloxy groups formed by substituting at least one hydrogen atom of each of the above-mentioned aryloxy groups with a substituent such as an alkyl group, a cycloalkyl group, an alkyl halide group, an alkoxy group, a halogen atom, an amino group, and an alkyl-substituted amino group, and also include aryloxy groups formed by substituting two adjacent hydrogen atoms of each of the above-mentioned aryloxy groups with a substituent such as an alkylenedioxy group.

Examples of a substituted silyl group include silyl groups formed by substituting at least one hydrogen atom of a silyl group with a substituent such as an alkyl group, a cycloalkyl group, an alkyl halide group, an alkoxy group, a halogen atom, an amino group, and an alkyl-substituted amino group.

The above-mentioned substituents, namely the substituents of a substituted alkyl group, a substituted cycloalkyl group, a substituted aralkyl group, a substituted aryl group, a substituted aliphatic heterocyclic group, a substituted aromatic heterocyclic group, a substituted alkoxy group, a substituted aralkyloxy group, a substituted aryloxy group and a substituted amino group, will be described in the following.

An alkyl group, a cycloalkyl group and an alkoxy group are the same as above-mentioned. Examples of a halogen atom include a fluorine atom, a chlorine atom, a bromine atom, an iodine atom, and the like.

Examples of an alkylenedioxy group include alkylenedioxy groups having a number of carbon atoms from 1 to 3. More specifically, the examples include a methylenedioxy group, an ethylenedioxy group, a propylenedioxy group, a trimethylenedioxy group, and the like.

Examples of an alkyl halide group include alkyl halides having a number of carbon atoms from 1 to 6 formed by halogenating (for example, fluorinating, chlorinating, bromining, iodinating, or the like) the above-mentioned alkyl groups. More specifically, the examples include a chloromethyl group, a bromomethyl group, a trifluoromethyl group, a 2-chloroethyl group, a 3-chloropropyl group, a 3-bromopropyl group, a 3,3,3-trifluoropropyl group, and the like.

Examples of an alkyl-substituted amino group include amino groups formed by substituting one or tow hydrogen atoms of each of the amino groups with an above-mentioned alkyl group and/or an above-mentioned cycloalkyl group. Specific examples of the alkyl-substituted amino group include monosubstituted amino groups such as a methylamino group, an ethylamino group, a propylamino group, a butylamino group, a penhtylamino group, and a hexylamino group, and disubstituted amino groups such as a dimethylamino group, a diethylamino group, a dipropylamino group, a dibutylamino group, a dipentylamino group, and a dihexylamino group.

Examples of a protective group include anything that can be used as an amino protective group, such as those described as amino protective groups in "Protective Groups in Organic Synthesis," second edition (John Wiley & Sons, Inc.). Specific examples of an amino protective group include an alkyl group, a cycloalkyl group, an aralkyl group, an acyl group, an alkyloxy carbonyl group, and the like.

An alkyl group, a cycloalkyl group and an alkoxy group are the same as above-mentioned. An acyl group may be in the form of a straight-chain, a branch or a ring. Examples include acyl groups having a number of carbon atoms from 2 to 7 that originate from a carboxylic acid. More specifically, the examples include an acetyl group, a propionyl group, a butyryl group, a pentanoyl group, a hexanoyl group, a benzoyl group, and the like. Examples of an alkyloxy carbonyl group include a tert-butyloxy carbonyl group, a benzyloxy carbonyl group, and the like.

Examples of an amino group having a protective group include amino groups protected by the above-mentioned protective groups. Specific examples of the amino group include an acetylamino group, a benzoylamino group, a tert-butyloxy carbonyl amino group, a benzyloxy carbonyl amino group, and the like.

Examples of a cyclic amino group include cyclic amines formed by binding alkylene chains such as a butylene group and a pentylene group, —CH$_2$CH$_2$OCH$_2$CH$_2$—, —CH$_2$CH$_2$NHCH$_2$CH$_2$—, —CH$_2$CH$_2$OCO—, and the like to a nitrogen atom. More specifically, the examples include a morpholino group, a piperidino group, a 1,3-oxazoline-2-on-1-yl group, and the like.

Next, an elimination group that is represented by E in general formula (1) will be explained. Examples of a carbonate ester represent by E include alkyl carbonate esters and benzyl carbonate esters such as a methyl carbonate, an ethyl carbonate, isopropyl carbonate, and a tert-butyl carbonate.

Examples of a carboxylate ester that is represented by E in general formula (1) include an acetoxy group and a benzoyloxy group.

Examples of an ether that is represented by E in general formula (1) include alkoxy groups and benzyloxy groups such as a methoxy group, an ethoxy group, an isopropyl group and a tert-butoxy group.

Examples of a phosphate ester that is represented by E in general formula (1) include alkyl phosphate esters and benzyl phosphate esters such as a dimethyl phosphate and a diethyl phosphate.

Examples of a sulfonate ester that is represented by E in general formula (1) include a methanesulfonate ester, a p-toluenesulfonate ester and a trifluoromethanesulfonate ester.

An allyl compound represented by general formula (1) may be a trans- or a cis-isomer. However, since the two have different reaction activities and enantioselectivities, it is necessary to select a structural isomer that can more efficiently produce a desired target product.

In the manufacturing method of the present invention, an allyl compound as shown by general formula (1) reacts with a diboron compound as shown by general formula (2). An amount of the diboron compound shown by general formula (2), to be used in the reaction, depends on an amount of the allyl compound to be used in the reaction, container for the reaction, form of the reaction, economic efficiency, and the like. In general, a mole ratio of the diboron compound with respect to the allyl compound is preferably selected from the range from 0.5 to 100 times, or even more preferably selected from the range from 1 to 5 times.

There is no particular restriction with respect to the type of X in the diboron compound represented by general formula (2) as far as it is an atom having an isolated electron pair, such as an oxygen atom and a nitrogen atom. Since X has an isolated electron pair, the isolated electron pair interacts with an empty orbit of an adjacent boron atom, thereby making the reactivity of the diboron compound appropriate. The four Xs in general formula (2) may be identical or different. Two adjacent Xs may, or may not, form a ring via other atoms.

Examples of an atom group that forms a ring in the diboron compound shown by general formula (2) include the ones shown by below-listed formulas (2a)-(2c). Examples of an atom group that does not form a ring include the ones shown by below-listed formulas (2d)-(2f).

[Formulas (2a)-(2f)]

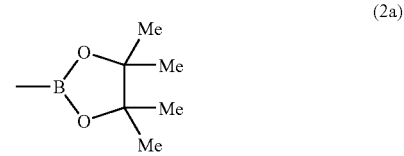

(2a)

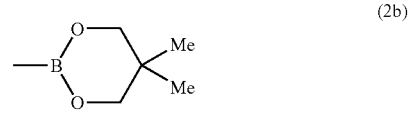

(2b)

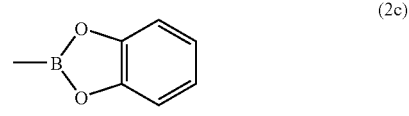

(2c)

(2d)

(2e)

(2f)

(where Ra and Rb represent identical or different alkyl or aryl groups, where the alkyl or aryl groups may be substituted.)

The reaction between the allyl compound shown by general formula (1) and the diboron compound shown by general formula (2) occurs in the presence of a catalyst. There is no particular restriction with respect to the catalyst as far as it is a material that has a catalytic capacity with respect to the reaction between the two. A monovalent copper complex, i.e., a copper (I) complex, is preferred in terms of reactivity. In particular, a copper (I) complex with a counter ion being an alkoxide or a hydride is preferred in that the reactivity becomes even better.

When the counter ion of the copper (I) complex is an alkoxide, examples of the alkoxide include a methoxide, an ethoxide, an isopropyloxide, and the like. In particular, a tert-butoxide is preferred in terms of reactivity.

When a copper (I) complex is used as a catalyst, it is preferred that the complex has a phosphine ligand so as to enable producing an optically active organoboron compound with a high enantioselectivity. Examples of the phosphine ligand include identical or different monodentate and bidentate ligands. In particular, a bidentate ligand is preferred.

Examples of a phosphine ligand include triphenylphosphine (TPP), 1,2-bis(diphenylphosphino)ethane (dppe), 1,3-bis(diphenylphosphino)propane (dppp), 1,4-bis(diphenylphosphino)butane (dppb), 1,1'-bis(diphenylphosphino)ferrocene (dppf), racemic Tol-BINAP, and the like.

In particular, as a phosphine ligand, an optically active compound represented by below-listed general formula (5) (hereafter, this compound is also referred to as Xantphos) is preferred in that it enables a high yield of an organoboron compound.

[General formula (5)]

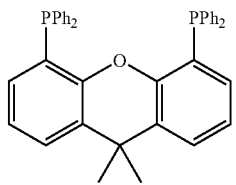

Further, a chiral phosphine ligand is preferred as a phosphine ligand in that it enables producing, with a high enantioselectivity, an optically active organoboron compound.

Examples of a chiral phosphine ligand include a cyclohexylanisylmethyl phosphine (CAMP), a 1,2-bis(anisylphenylphosphino)ethane (DIPAMP), 1,2-bis(alkylmethylphosphino)ethane (BisP*), a 2,3-bis(diphenylphosphino)butane (CHIRAPHOS), a 1,2-bis(diphenylphosphino)propane (PROPHOS), a 2,3-bis(diphenylphosphino)-5-norbornene (NORPHOS), a 2,3-O-isopropylidene-2,3-dihydroxy-1,4-bis (diphenylphosphino)butane (DIOP), a 1-cyclohexyl-1,2-bis (diphenylphosphino)ethane (CYCPHOS), a 1-substituted-3, 4-bis(diphenylphosphino)pyrrolidine (DEGPHOS), a 2,4-bis-(diphenylphosphino)pentane (SKEWPHOS), a 1,2-bis (substituted phospholano)benzene (DuPHOS), a 1,2-bis (substituted phopholano)ethane (BPE), a 1-(substituted phospholano)-2-(diphenylphosphino)benzene (UCAP-Ph), a 1-(bis(3,5-dimethyl)phophino)-2-(substituted phospholano) benzene (UCAP-DM), a 1-((substituted phospholano)-2-(bis (3,5-di(t-butyl)-4-methoxyphenyl)phosphino)benzene (UCAP-DTBM), a 1-((substituted phospholano)-2-(di-naphthalen-1-yl-phosphino)benzene (UCAP-(1-Nap)), a 1-[1',2-bis(diphenylphosphino)ferrocenyl]ethylamine (BPPFA), a 1-[1',2-bis(diphenylphosphino)ferrocenyl]ethyl alcohol (BPPFOH), a 2,2'-bis(diphenylphosphino)-1,1'-dicyclopentane (BICP), a 2,2'-bis(diphenylphosphino)-1,1'-binaphthyl (BINAP), a 2,2'-bis(diphenylphosphino)-1,1'-(5,5',6,6',7,7',8, 8',-octahydro binaphthyl (H$_8$-BINAP), a 2,2'-bis(di-p-tolylphosphino)-1,1'-binaphthyl (TOL-BINAP), a 2,2'-bis(di (3,5-dimethylphenyl)phosphino)-1,1'-binaphthyl (DM-BINAP), a 2,2'-bis(diphenylphosphino)-6,6'-dimethyl-1,1'-biphenyl (BICHEP), a ((5,6),(5',6')-bis(methylenedioxy) biphenyl-2,2'-diyl)(bisdiphenylphosphine) (SEGPHOS), a ((5,6),(5',6')-bis(methylenedioxy)biphenyl-2,2'-diyl)(bis(3, 5-dimethylphenyl)phosphine) (DM-SEGPHOS), a ((5,6),(5', 6')-bis(methylenedioxy)biphenyl-2,2'-diyl)(bis(3,5-di(tert-butyl)-4-methoxyphenyl)phosphine) (DTBM-SEGPHOS), and the like.

In particular, as a phosphine ligand, a 2,3-bis(alkylmethylphosphino) quinoxaline, which is an optically active phosphine represented by below-listed general formula (6) (hereafter, this compound is also referred to as Quinox P), is preferred in that it enables producing, with a high enantioselectivity, an optically active organoboron compound.

[General formula (6)]

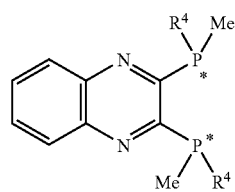

(where $R^4$ represents a bulky alkyl group, and * represents a chiral atom.)

Examples of a bulky alkyl group represented by $R^4$ in general formula (6) include an isopropyl group, a tert-butyl group, a cyclohexyl group, an adamantyl group and a 1, 1,3,3-tetramethylbutyl group. A tert-butyl group is preferred in terms of availability.

An amount of the catalyst in the present invention, to be used in the reaction, depends on the type of the allyl compound to be used in the reaction, container for the reaction, form of the reaction, economic efficiency, and the like. In general, a mole ratio of the catalyst with respect to the allyl compound is preferably selected from the range from 1/100, 000 to 1/2 times, or even more preferably selected from the range from 1/1,000 to 1/10 times.

The manufacturing method of the present invention, as needed, can be performed in a solvent. The solvent is preferred to be a substance that can solve an allyl compound, which is the starting material, and an organoboron compound, which is the product, and that does not react with each of the reactants.

Specific examples of the solvent include an aromatic hydrocarbon such as a benzene, a toluene, and a xylene; an aliphatic hydrocarbon such as a pentane, a hexane, a heptane, and an octane; a halogenated hydrocarbon such as an ethylene chloride, a chloroform, a carbon tetrachloride, and a dichloroethane; an ether such as a diethyl ether, a diisopropyl ether, a tert-butylmethyl ether, a dimethoxyethane, a tetrahydrofuran (THF), a tetrahydropyran (THP), a dioxin, and a dioxolan; an amide such as an N,N-dimethylformamide (DMF) and an N,N-dimethylacetamide (DMA); an acetonitrile; an N-methylpyrrolidone (NMP); a dimethylsulfoxide (DMSO), and a dimethylimidazolidinone (DMI). These solvents may be used either alone or in combination of two or more. Among these solvents, THF, toluene, and DMI are particularly preferred.

An amount of the solvent depends on an solubility of the allyl compound, which is the starting material, and economic efficiency. For example, when a tetrahydrofuran is used as the solvent, depending on the starting material to be used, the reaction can be performed in a solvent of low concentration of below 0.01 mass %, without a solvent, or in a state of almost without a solvent. In general, the amount of the solvent to be used is in the range from 0.05 to 10 mass %, or more preferably in the range from 0.10 to 5 mass %.

(4). In terms of reaction mechanism, the two types of compounds are the same in that displacement of a hydrogen atom and bond dislocation are involved in a conjugate group in both. Therefore, there is no essential difference between the two.

For example, when an allyl compound shown by general formula (1) in which R is a —$C_2H_4$Ph and E is a —$CH_2OCO_2$Me in general formula (1) and a copper (I) alkoxy complex coordinated with a bidentate phosphine ligand is used as a catalyst, the inventors of the present invention speculate that an allylboron compound is produced according to the following reaction mechanism.

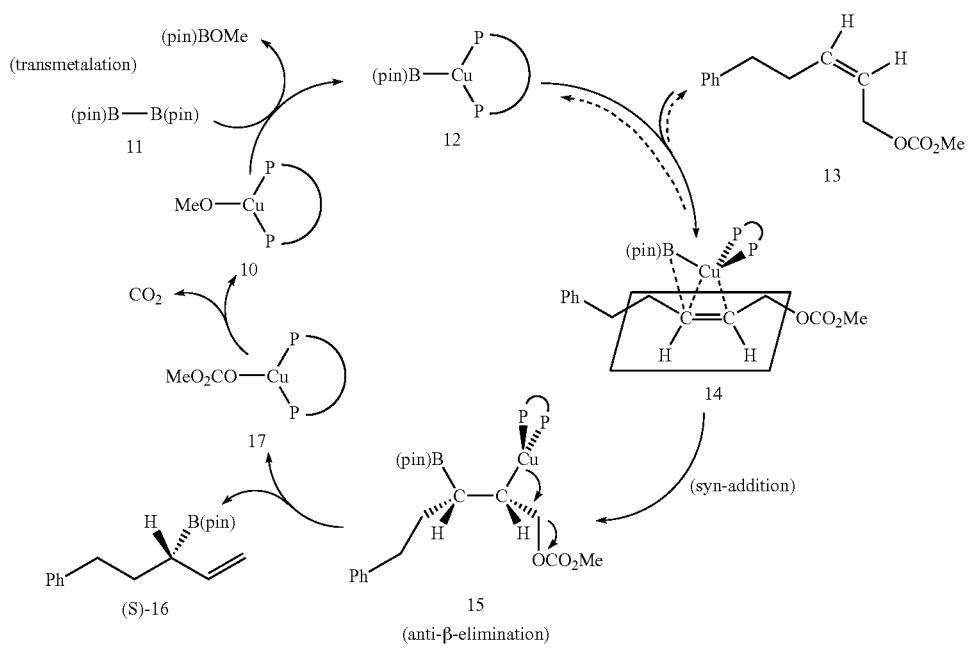

Reaction temperature is generally set, in the range from −80 to 100° C., or more preferably in the range from 0 to 30° C., considering economic efficiency, and the like.

Reaction time depends on type and amount of a catalyst to be used, type and concentration of a starting material to be used, and reaction conditions such as reaction temperature. In general, the reaction proceeds for a period from a few minutes to a few tens of hours. In general, the reaction time is set in the range from 1 minutes to 1 month, or more preferably from 10 minutes to 48 hours.

The manufacturing method of the present invention can be performed with either a batch-wise or continuous-wise reaction form.

An organoboron compound produced by using the manufacturing method of the present invention is used as an intermediate material of a medicine, an agricultural chemical or a biologically active substance. For example, it is useful as a synthetic intermediate of an antibiotic substance. The types of the organoboron compound produced by using the manufacturing method of the present invention can be largely divided into an allylboron compound type shown by general formula (3) and a boryl cyclopropane type shown by general formula In the above reaction mechanism, first, a carbon-carbon double bond of allyl compound 13 is coordinated with respect to boryl copper intermediate 12, which is produced from alkoxy copper 10 and diboron 11, to produce coordinate complex 14. In this case, copper center takes a tetrahedral structure, and the carbon-carbon double bond is parallel to a boron-copper (I) bond, so that a geometry in which copper is located at the β position of an elimination group of allyl compound 13 is most stable. Thereafter, boron and copper are syn-added to produce alkyl copper intermediate 15. Next, copper and elimination group are anti-β-eliminated to produce alkylboron compound (S)-16, which is the target product. Simultaneously produced copper carbonate complex 17 decarboxylates, by which, alkoxy copper 10 and diboron 11 are produced. Boryl copper intermediate 12 is reproduced by transmetalation of alkoxy copper 10 and diboron 11.

On the other hand, when an allyl compound shown by general formula (1) in which R is a —Si($CH_3$)$_3$ and E is a —$CH_2OCO_2$Me is used and a copper (I) alkoxy complex coordinated with a bidentate phosphine ligand is used as a catalyst, the inventors of the present invention speculate that a boryl cyclopropane compound is produced according to the following reaction mechanism.

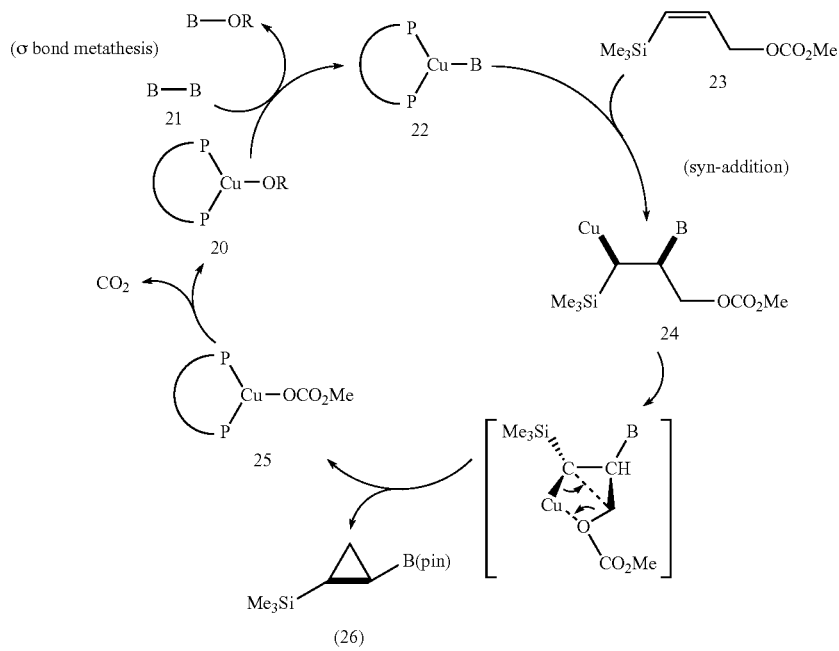

In the above reaction mechanism, first, by a metathesis reaction between alkoxy copper 20, which is a catalyst precursor, and diboron 21, boryl copper complex 22, which is an active species in a catalytic cycle, is produced. Boryl copper 22 is added to a double bond of allyl compound 23. The addition is speculated to be a syn-addition. Alkyl copper intermediate 24, which is produced by the addition, undergoes a ring-closing reaction, accompanied by elimination of copper carbonate compound 25. Thereby, boryl cyclopropane compound 26, which is the target product, is produced. Copper carbonate compound 25, which was produced simultaneously with boryl cyclopropane compound 26, decarboxylates to reproduce alkoxy copper 20.

In the manufacturing method of the present invention, whether an allylboron compound represented by general formula (3) or a boryl cyclopropane represented by general formula (4) is more produced than the other depends on the structure of an allyl compound, which is the starting material. For example, as an allyl compound represented by general formula (1), when R in general formula (1) is an aralkyl group or a substituted aralkyl group, an optically active allylboron compound represented by general formula (3) is primarily produced. On the other hand, as an allyl compound represented by general formula (1), when R in general formula (1) is an aryl group, a substituted aryl group, or a substituted silyl group, a racemic or optically active boryl cyclopropane compound represented by general formula (4) is primarily produced.

In the manufacturing method of the present invention, when one wants to selectively produce either an allylboron compound represented by general formula (3) or a boryl cyclopropane compound represented by general formula (4), he or she may suitably select a catalyst, a solvent, and manufacturing conditions that allow a more favorable product ratio. Or, one may produce a mixture of an allylboron compound represented by general formula (3) and a boryl cyclopropane compound represented by general formula (4), and then, isolate a desired organoboron compound by crystallization, distillation, column chromatography, preparative HPLC, or the like.

In the manufacturing method of the present invention, a boryl cyclopropane compound represented by general formula (4) is racemic or optically active. The boryl cyclopropane compound structurally can be both a trans-isomer and a cis-isomer. From the experience of the present inventors, there is a tendency that the trans-isomer is a slightly richer mixture. When one wants to selectively produce either the trans-isomer or the cis-isomer, he or she may suitably select a catalyst, a solvent, and manufacturing conditions that allow a more favorable product ratio. Or, one may produce a mixture of a trans-isomer and a cis-isomer, and then, isolate a desired isomer by crystallization, distillation, column chromatography, preparative HPLC, or the like.

The manufacturing method of an organoboron compound of the present invention, being a manufacturing process having a superior reaction catalyst activity and/or optical selectivity, allows producing a desired organoboron compound with a short-step, and is therefore industrially highly useful.

Embodiments

The present invention is further explained in detail in the following by using embodiments. The embodiments are merely for exemplification purposes, and the invention is not limited to these embodiments.

All synthesis processes were performed by using test tubes sealed with teflon (registered trademark) coated rubber septum. The test tubes were dried via heating-vacuuming-cooling. Reaction was performed in an argon or nitrogen atmosphere.

Phosphine ligand Xantphos was prepared according to the procedure of Organometallics, vol. 14 (1995), pages 3081-3089. Copper (I) complex Cu(O-t-Bu) was prepared according to Inorg. Chem., vol. 29 (1990), pages 3680-3685 by vacuum sublimating a mixture of CuCl and Li(O-t-Bu). QuinoxP marketed by Sigma-Aldrich Corporation was used. Other phosphine ligands were bought from Strem Chemicals, Inc. Solvent was of a dehydration class bought from Kanto Chemical Co., Inc., which was further deaerated by using a frozen-melt method and dehydrated with a Molecular Sieve 4A.

An Varian Gemini 2000 (1H; 300 MHz, 13C; 75.4 MHz, 31P; 121.4 MHz) NMR apparatus was used for taking NMR spectrum. A tetramethylsilane (1H) and a heavy chloroform (13C) were used as an internal reference, and an 85% phosphoric acid was used as an external reference. A Shimadzu GC-14B FID detector was used for chromatography. Mass spectra was measured with a Joel JMS700TZ by using a ESI or APCI method.

Starting material, an allyl compound represented by general formula (1), was prepared from corresponding allyl alcohol according to Related Art 3 by using a standard procedure.

Embodiment 1

Synthesis of 4,5,5,5-tetramethyl-2-[(3S)-5-phenyl-1-pentene-3-yl]-1,3,2-dioxaborolan In a glove box in an argon atmosphere, Cu (O-t-Bu) (3.4 mg, 0.025 mmol), (R,R)-bis(tert-butylmethylphosphino)quinoxaline (abbreviated as (R,R)-QuinoxP) (8.4 mg, 0.025 mmol) were put into a vial container, dried THF (0.5 mL) was added, and stirred to make a yellow-colored slurry. When a bis(pinacolato)diboron (254 mg, 1.0 mmol) was added, the mixture changed from a yellow color to a red-purple color. When an allyl compound (methyl carbonate-5-phenyl-2-pentene-1-yl ester) (0.5 mmol) was added to the mixture, gas was generated, and a slight increase in internal temperature in a 30-minute period was observed. After reaction, the reaction mixture was directly subjected to column chromatography (SiO2, hexane:acetic ether=95.5:0.5-95:5), and the titled organoboron compound was obtained. Identification data is as follows. 1H-NMR (CDl3, δ): 1.24 (s, 12H), 1.66-1.83 (m, 1H), 1.83-1.95 (m, 2H), 2.51-2.73 (m, 2H), 4.96-5.07 (m, 2H), 5.75-5.90 (m, 1H), 7.12-7.30 (m, 5H), 13C-NMR (CDl3,δ): 24.5, 24.6, 29.8 (br), 32.1, 35.1, 83.2, 114.1, 125.7, 128.3, 128.6, 139.3, 142.8. [α] 29.5 D=−5.12 (c, 1.04, CHCl3), IR (neat, cm-1): 3027 (m), 2978 (m), 2928 (m), 1631 (m), 1320 (s), 1141 (s). HRMS-APCI (m/z): [M+Na]+ calcd for C17H25O2BNa, 295.1845; found, 295.1836.

Embodiments 2-11

By making various changes to an allyl compound, a phosphine ligand, a solvent, and the like, optically active allylboron compounds were obtained according to the same procedure as Embodiment 1, and the results were collectively shown in table 1, where pin denotes pinacolato (the same notation is used in all of the following tables).

TABLE 1

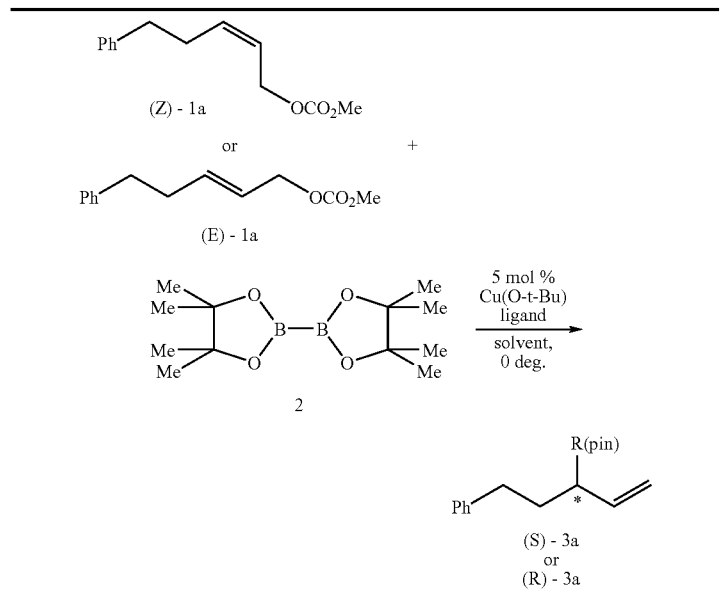

| Embodiment | Starting material | Ligand | Solvent | Time (h) | Yield (%)b (1h-NMR) | ee(%)c (steric) |
|---|---|---|---|---|---|---|
| 1 | (Z)-1a | (R,R)-QuinoxP | THP | 20 | 77 | 94 (S) |
| 2 | (Z)-1a | (R,R)-Me-Duphos | THP | 3 | 97 | 80 (S) |
| 3 | (Z)-1a | (R,R)-i-Pr-Duphos | toluene | 20 | 72 | 79 (S) |
| 4 | (Z)-1a | (R,R)-DIOP | THP | 20 | 59 | 37 (S) |
| 5 | (Z)-1a | (R,R)-BINAP | THP | 20 | 16 | 31 (S) |
| 6 | (Z)-1a | (R,R)-QuinoxP | THP | 20 | 85 | 95 (S) |
| 7 | (Z)-1a | (R,R)-QuinoxP | toluene | 20 | 78 | 96 (S) |

TABLE 1-continued

| | | | | | | |
|---|---|---|---|---|---|---|
| 8d | (Z)-1a | (R,R)-QuinoxP | DMI | 20 | 55 | 94 (S) |
| 9 | (E)-1a | (R,R)-QuinoxP | THP | 20 | 94 | 44 (S) |
| 10 | (E)-1a | (R,R)-Me-Duphos | THP | 3 | 97 | 6 (S) |
| 11 | (E)-1a | (R,R)-i-Pr-Duphos | toluene | 20 | 68 | 23 (S) | a condition: catalyst (5 mol %), ligand (5 mol %), allyl compound 1a (0.5 mmol).

b yield determined by 1H-NMR.

c ee value of an allylboron compound determined by analyzing, with a chiral GLC, a trifluoroacetic derivative of an alcohol obtained by oxidizing 3a with H2O2/H2O.

d reaction temperature is room temperature.

Embodiments 12-15

By making various changes to an allyl compound, boryl cyclopropane and allylboron compounds were obtained according to the same procedure as Embodiment 1, and the results were collectively shown in table 1.

TABLE 2

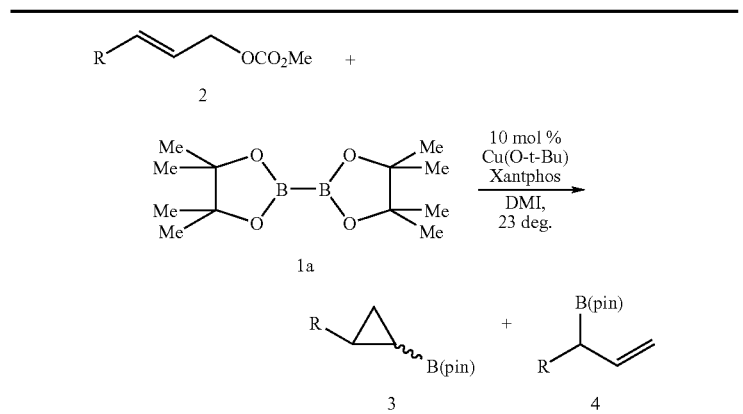

| | | | Yield (%) b | | Isomer ration of 3 |
|---|---|---|---|---|---|
| Embodiment | R | Alkene naming | Time (h) | 3 | 4 | Trans:cis c |
| 12 | Me3Si | (E)-2 a | 29 | 60 | 17 | 87:13 |
| 13 | PhMe2Si | (E)-2 b | 27 | 62 | 8 | 93:7 |
| 14 | Ph2MeSi | (E)-2 c | 30 | 68 | Trace | 80:20 |
| 15 d | Me2(i-PrO)Si | (E)-2 d | 10 | 76 | 4 | 97:3 | a condition: catalyst (10 mol %), allyl compound 2 (0.25 mmol), diboron 1a (0.45 mmol), solvent (0.25 ml).

b yield determined by 1H-NMR using 1,1,2,2-tetrachloroethane as an internal reference.

c ratio determined by GC.

d performed on a 0.15 mmol scale.

In table 2, the allyl compound was synthesized from corresponding allyl alcohol according to Related Art 3 by using a standard procedure.

With respect to the allyl compound ((E)-2b) used in embodiment 13, the chemical name of this compound is (E)-3-(dimethylphenylsilyl)-2-propene-1-yl methyl carbonate ester. Identification data is as follows. 1H-NMR (CDC13, δ) 0.35 (s, 6H), 3.80 (s, 3H), 4.68 (t, J=1.5 Hz, 2H), 6.12 (dd, J=1.8 Hz, 2H), 7.35-7.52 (m, 5H), 13C-NMR (CDC13, δ) −3.0, 54.8, 69.9, 127.9, 129.2, 131.7, 133.9, 138.0, 140.4, 155.7.

With respect to the boryl cyclopropane ((E)-3b) obtained in embodiment 13, the chemical name of this compound is 2-[(E)-2-(dimethylphenylsilyl)cyclopropyl]-4,4,5,5-tetramethyl-1,3,2-dioxaborolan. Identification data is as follows. 1H-NMR (CDC13, δ) −0.17 (ddd, 3J=5.8, 7.1, 8.3 Hz, 1H), −0.076 (ddd, 3J=8.3, 8.5, 9.4 Hz, 1H), 0.18 (d, J=4.4 Hz, 6H), 0.56 (ddd, 3J=7.1, 8.5 Hz, 2J=3.0 Hz, 1H), 0.87 (ddd, 3J=5.8, 9.4 Hz, 2J=3.0 Hz, 1H), 1.22(s, 12H), 13C-NMR (CDC13, δ) −4.4, −4.1, 2.3, 7.8, 24.5, 24.6, 82.9, 127.7, 128.9, 134.0, 139.0.

With respect to the allyl compound ((E)-2c) used in embodiment 14, the chemical name of this compound is (E)-3-(diphenylmethylsilyl)-2-propene-1-yl methyl carbonate ester. Identification data is as follows. 1H-NMR (CDC13, δ) 0.63 (s, 3H), 3.80 (s, 3H), 4.7 (d, J=4.2 Hz, 2H), 6.1-6.3 (m, 2H), 7.4-7.5 (m, 10H), 13C-NMR (CDC13, δ) −4.2, 54.7, 69.6, 127.9, 129.1, 129.5, 134.8, 135.8, 142.5, 155.6.

With respect to the boryl cyclopropane ((E)-3c) obtained in embodiment 14, the chemical name of this compound is 2-[(E)-2-(diphenylmethylsilyl)cyclopropyl]-4,4,5,5-tetramethyl-1,3,2-dioxaborolan. Identification data is as follows. 1H-NMR (CDC13, δ) −0.15 (ddd, 3J=5.8, 8.7, 9.4 Hz, 1H), −0.35 (ddd, 3J=7.0, 8.7, 9.4 Hz, 1H), 0.45 (s, 3H), 0.56 (ddd, 3J=7.0, 8.7 Hz, 2J=3.0 Hz, 1H), 0.96 (ddd, 3J=5.8, 9.3 Hz, 2J=3.0 Hz, 1H), 1.23 (s, 12H), 13C-NMR (CDC13, δ) −5.6, −3.0, 1.0, 7.7, 24.5, 24.6, 83.0, 127.71, 127.73, 129.23, 129.26, 135.0, 136.57, 136.60.

With respect to the allyl compound ((E)-2d) used in embodiment 15, the chemical name of this compound is (E)-3-(dimethyl(2-propyloxy)silyl)-2-propene-1-yl methyl carbonate ester. This compound was synthesized by using a reaction described in Org. Lett. Vol. 7 (2005) pages 3001-3004. Identification data is as follows. 1H-NMR (CDC13, δ) 0.20 (s, 6H), 1.15 (d, J=6.3 Hz, 6H), 3.81 (s, 3H), 4.0 (sept, J=6.1 Hz, 1H), 4.68 (dd, J=4.8, 1.4 Hz, 2H), 5.94-6.00 (dd, J=5.9, 1.1 Hz, 1H), 6.20 (dt, J=4.7, 8.9 Hz, 1H), 13C-NMR (CDC13, δ) −1.6, 25.6, 54.8, 65.1, 69.7, 131.6, 140.4, 155.6.

With respect to the boryl cyclopropane ((E)-3d) obtained in embodiment 15, the chemical name of this compound is 2-[(E)-2-[dimethyl(2-propyloxy)silyl]cyclopropyl]-4,4,5,5-tetramethyl-1,3,2-dioxaborolan.

Embodiments 16-22

By making various changes to an allyl compound, a catalyst and a solvent, boryl cyclopropane and allylboron compounds were obtained according to the same procedure as Embodiment 1, and the results were collectively shown in table 3.

TABLE 3

| | | | | Yield (%) b | | Isomer ratio of 3 |
| Embodiments | Ligand | Solvent | Time (h) | 3 | 4 c | Trans:cis c |
|---|---|---|---|---|---|---|
| 16 | Xantphos | THF | 1 | 96 | 1 | >99:1 |
| 17 d | Xantphos | THF | 2 | 96 (84) e | 1 | >99:1 |
| 18 | PPh3 | THF | 24 | 12 | Trase | >99:1 |
| 19 | Xantphos | DMI | 1 | 98 | 1 | >99:1 |
| 20 | Xantphos | toluene | 2 | 98 | 1 | >99:1 |
| 21 | Xantphos | THP | 2 | 98 | 1 | >99:1 |
| 22 f | Xantphos | DMI | 28 | 85 | 1 | >99:1 | a condition: catalyst (3 mol %), allyl compound 2a (0.25 mmol), diboron 1a (0.50 mmol), solvent (0.125 ml).
b yield determined by GC.
c ratio with respect to yield determined by GC.
d performed on a 2.0 mmol (1a) scale.
e isolation yield.
f catalyst of 1 mol % used at 28° C.
d reaction temperature is room temperature.

With respect to the allyl compound ((Z)-2a) used in embodiment 16, the chemical name of this compound is (Z)-3-(trimethylsilyl)-2-propene-1-yl methyl carbonate ester. Identification data is as follows. 1H-NMR (CDC13, δ) 0.15 (d, J=0.6 Hz, 9H), 3.80 (d, J=0.9 Hz, 3H), 4.70 (d, J=6.6 Hz, 2H), (s, 6H), 5.85 (dd, J=15, 1 Hz, 1H), 6.40 (ddt, J=15, 6.6, 1 Hz, 1H), 13C-NMR (CDC13, δ) −0.30, 54.7, 67.6, 135.3, 140.4, 155.8, IR (neat, cm-1) 2958 (m), 1749 (s), 1614 (l), 1443 (m), 1347 (m), 1248 (s), 959 (m), 836 (s), 764 (m).

Embodiments 23 and 24

By making changes to an allyl compound and using a chiral catalyst as a catalyst, optically active boryl cyclopropane and allylboron compounds were obtained according to the same procedure as Embodiment 1, and the results were collectively shown in table 4.

TABLE 4

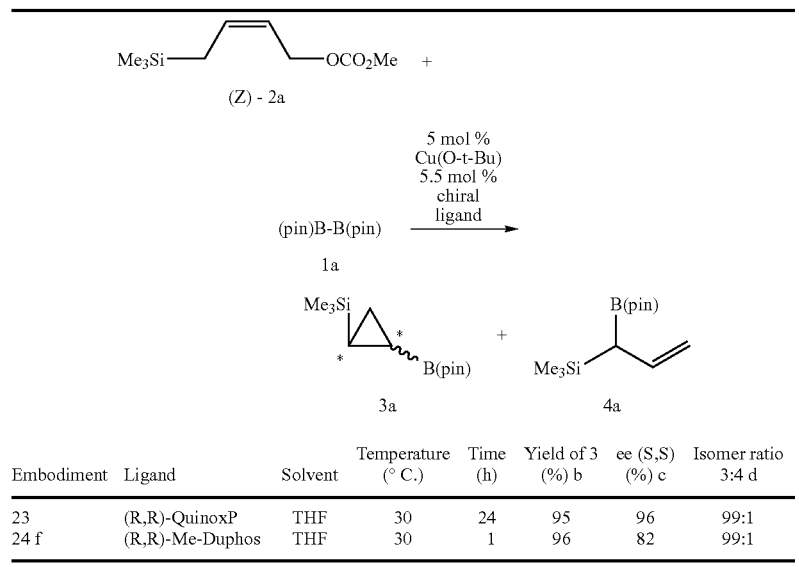

| Embodiment | Ligand | Solvent | Temperature (° C.) | Time (h) | Yield of 3 (%) b | ee (S,S) (%) c | Isomer ratio 3:4 d |
|---|---|---|---|---|---|---|---|
| 23 | (R,R)-QuinoxP | THF | 30 | 24 | 95 | 96 | 99:1 |
| 24 f | (R,R)-Me-Duphos | THF | 30 | 1 | 96 | 82 | 99:1 | a condition: catalyst (5 mol %), allyl compound 2a (0.25 mmol), diboron 1a (0.50 mmol), solvent (0.125 ml).
b yield determined by GC.
c determined by chiral GC.
d determined by chiral GC.

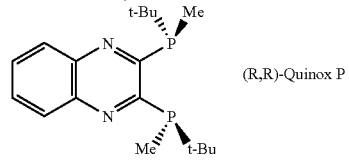

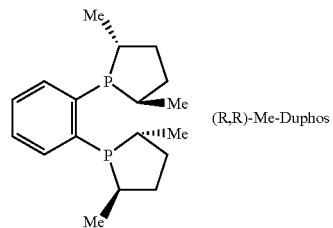

With respect to the optically active boryl cyclopropane ((S,S)-3a) obtained in embodiment 23, the chemical name of this compound is (1S, 2S)-2-[(E)-2-[trimethylsilyl]cyclopropyl]-4,4,5,5-tetramethyl-1,3,2-dioxaborolan. Identification data is as follows. 1H-NMR (CDC13, δ) −0.27 (ddd, 3J=5.5, 5.6, 8.25 Hz, 1H), −0.15 (m, 1H), −0.068 (s, 9H), 0.51 (ddd, 3J=7.1, 8.25 Hz, 2J=2.7 Hz, 1H), 0.78 (ddd, 3J=5.6, 9.5 Hz, 2J=2.7 Hz, 1H), 1.22 (s, 12H), 13C-NMR (CDC13, δ) −2.8, −2.9, 3.4, 7.7, 24.5, 82.8.

ee-purity of (1S, 2S)-3a was determined by chiral GC analysis (Chiradex G-TA, 65° C., (S,S) isomer: t=47.0 minutes, (R,R) isomer: t=58.8 minutes) [α] 19D=+24.4 (c 1.2, CHC13).

The absolute configuration of the optically active boryl cyclopropane ((S,S)-3a) obtained in embodiment 23 was determined by using the new Mosher method. A sample was hydrogen peroxide oxidated to give an alcohol, and (R)- and (S)-esters were induced from (−)- and (+)-MTPA chlorides. That the main product is an (S,S)-isomer was determined analyzing an 1H-NMR chart of each of the MTPA esters.

Embodiments 25-35

By making various changes to an allyl compound, a catalyst and a solvent, boryl cyclopropane compounds were obtained according to the same procedure as Embodiment 1, and the results were collectively shown in table 5.

TABLE 5

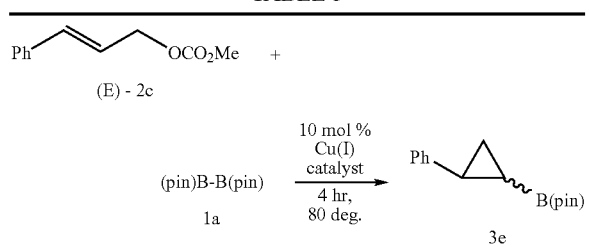

TABLE 5-continued

| Embodiment | Catalyst | Solvent | Yield (%) c | Isomer ratio of 3 trans:cis d |
|---|---|---|---|---|
| 25 b,e | Cu(O-t-Bu)-Xantphos | DMI | 86 | 97:3 |
| 26 b | [Ph3P-CuH]6-Xantphos | DMI | 87 | 97:3 |
| 27 | Cu(O-t-Bu)-dppe | DMI | 17 | >99:1 |
| 28 | Cu(O-t-Bu)-dppp | DMI | 11 | 85:15 |
| 29 | Cu(O-t-Bu)-dppb | DMI | 24 | 87:13 |
| 30 | Cu(O-t-Bu)-dppf | DMI | 39 | 95:5 |
| 31 | Cu(O-t-Bu)-(S)-Tol-BINAP | DMI | 19 | >99:1 |
| 32 b | Cu(O-t-Bu)-Xantphos | DMA | 70 | 96:4 |
| 33 b | Cu(O-t-Bu)-Xantphos | NMF | 76 | 97:3 |
| 34 b | Cu(O-t-Bu)-Xantphos | DMP | 75 | 97:3 |
| 35 b | [Ph3P-CuH]6-Xantphos | toluene | 77 | 91:9 | a condition: catalyst (10 mol %), allyl compound 2 (0.20 mmol), diboron 1a (0.36 mmol), solvent (0.20 ml).
b 2 (0.25 mmol), 1a (0.50 mmol), solvent (0.25 ml).
c yield determined by GC.
d determined by chiral GC.
e isolation yield was 73% (0.5 mmol scale).

With respect to the boryl cyclopropane ((E)-3e) obtained in embodiment 25, the chemical name of this compound is 2-[(E)-2-phenylcyclopropyl]-4,4,5,5-tetramethyl-1,3,2-dioxaborolan. Identification data is as follows. 1H-NMR (CDC13, δ) 0.30 (ddd, 3J=5.5, 6.8, 9.7 Hz, 1H), 1.01 (ddd, 3J=5.3, 9.7 Hz, 2J=3.7 Hz, 1H), 1.16 (ddd, 3J=6.8, 9.7 Hz, 2J=3.7 Hz, 1H), 1.25(s, 12H), 2.10 (ddd, 3J=6.8, 9.7 Hz, 3.7 Hz, 1H), 7.07-7.27 (m, 5H), 13C-NMR (CDC13, δ) 4.5, 14.9, 21.7, 24.5, 24.6, 83.1, 125.6, 125.7, 128.3, 143.5, IR (neat, cm-1) 3027 (s), 2978 (m), 2931 (s), 1605 (m), 1418 (l), 1356 (l), 1319 (l), 1216 (l), 1142 (l), 859 (l), 760 (m), 750 (m), 696 (l), 670 (l).

Embodiments 36-42

By making various changes to an allyl compound and a catalyst, boryl cyclopropane compounds were obtained according to the same procedure as Embodiment 1, and the results were collectively shown in table 6.

TABLE 6

| Embodiment | R | Time (h) | Yield (%) c | Isomer ratio of 3 trans:cis d |
|---|---|---|---|---|
| 36 | MeOCO | 4 | 86 | 97:3 |
| 37 | i-PrOCO | 4 | 80 | 91:9 |
| 38 b | t-BuOCO | 15 | 60 | 96:4 |
| 39 | MeCO | 1 | 10 | Nd |
| 40 | PhCO | 1 | 28 | 91:9 |
| 41 | Me | 1 | 21 | 96:4 |
| 42 c | (EtO)2OP | 3 | 70 | 71:29 | a, b catalyst (10 mol %).
a allyl compound 2 (0.25 mmol), diboron 1a (0.50 mmol), solvent (0.25 ml).
b allyl compound 2 (0.20 mmol), diboron 1a (0.36 mmol), solvent (0.20 ml).
c allyl compound 2 (0.50 mmol), diboron 1a (1.0 mmol), solvent (0.25 ml).
d yield determined by GC.
e determined by GC.

Embodiments 43-55

By making various changes to an allyl compound and a catalyst, boryl cyclopropane compounds were obtained according to the same procedure as Embodiment 1, and the results were collectively shown in table 7.

TABLE 7

| Embodiment | E/Z | R | Alkene naming | Time (h) | Yield (%) b | Isomer ratio of 3 trans:cis c |
|---|---|---|---|---|---|---|
| 43 | E | Ph | (E)-2e | 5 | 73 | 97:3 |
| 44 | Z | Ph | (Z)-2e | 10 | 66 | 96:4 |
| 45 | E | p-Me-Ph | 2f | 3 | 62 | 96:4 |
| 46 | E | o-Me-Ph | 2g | 2 | 59 | 93:7 |
| 47 | E | 2,4-Me2-Ph | 2h | 22 | Trace | 95:5 |
| 48 | E | 2,4,6-Me3-Ph | 2i | 56 | 75 | Nd |
| 49 | E | p-MeO-Ph | (E)-2j | 3 | 41 | 80:20 |
| 50 | Z | p-MeO-Ph | (Z)-2j | 10 | 50 (67) d | 86:16 |
| 51 | E | p-F-Ph | 2k | 48 | N.R. | 95:5 |

TABLE 7-continued

| 52 | Z | p-Cl-Ph | (E)-2l | 48 | N.R. | Nd |
|----|---|---------|--------|----|------|-----|
| 53 | E | p-Cl-Ph | (Z)-2l | 99 | 0 | Nd |
| 54 | E | p-NO2-Ph | 2m | 22 | N.R. | Nd |
| 55 | E | 3-methyl-1-Boc-indol-2-yl | 2n | 27 | | Nd | a condition: catalyst (10 mol %), allyl compound 2 (0.50 mmol), diboron 1a (0.45 mmol), solvent (0.25 ml).
b isolation yield.
c ratio determined by GC.
d yield determined by NMR.
e determined by GC.

With respect to the allyl compound ((Z)-2e) used in embodiment 44, the chemical name of this compound is (Z)-3-phenyl-2-propene-1-yl methyl carbonate ester. This compound was synthesized according to J.A.C.S. 123 (2001) 12168-12175. Identification data is as follows. 1H-NMR (CDC13, δ) 3.80 (s, 3H), 4.91 (dd, J=1.6, 6.5Hz, 2H), 5.85 (dt, J=12, 6.6 Hz, 1H), 6.91 (d, J=12 Hz, 1H), 7.22-7.39 (m, 5H). 13C-NMR (CDC13, δ) 54.7, 64.7, 125.2, 127.7, 128.4, 128.7, 133.5, 135.9, 144.8.

With respect to the boryl cyclopropane ((E)-3f) obtained in embodiment 45, the chemical name of this compound is 2-[(E)-2-(4-methylphenyl)cyclopropyl]-4,4,5,5-tetramethyl-1,3,2-dioxaborolan. Identification data is as follows. 1H-NMR (CDC13, δ) 0.26 (ddd, 3J=5.4, 6.8, 9.6 Hz, 1H), 0.97 (ddd, 3J=5.2, 9.6 Hz, 2J=3.6 Hz, 1H), 1.12 (ddd, 3J=6.8, 8.1 Hz, 2J=3.6 Hz, 1H), 1.25 (d, J=3.8 Hz, 12H), 2.07 (ddd, 3J=5.2, 8.1, 3.6 Hz, 1H), 2.29 (s, 3H), 7.02 (dd, J=8.1, 23.1 Hz, 4H). 13C-NMR (CDC13, δ) 4.2, 14.7, 20.8, 21.5, 24.5, 24.6, 83.1, 125.7, 129.0, 135.1, 140.3, IR (neat, cm-1) 2978 (m), 2927 (m), 1518 (m), 1420 (l), 1407 (m), 1353 (l), 1319 (l), 1218 (m), 859 (l), 797 (m), 661 (m).

With respect to the boryl cyclopropane ((E)-3g) obtained in embodiment 46, the chemical name of this compound is 2-[(E)-2-(2-methylphenyl)cyclopropyl]-4,4,5,5-tetramethyl-1,3,2-dioxaborolan. Identification data is as follows. 1H-NMR (CDC13, δ) 0.15 (ddd, 3J=5.9, 6.4, 9.5 Hz, 1H), 1.01 (ddd, 3J=5.7, 9.5 Hz, 2J=3.6 Hz, 1H), 1.13 (ddd, 3J=6.4, 8.0 Hz, 2J=3.6 Hz, 1H), 1.26 (s, 12H), 2.09 (ddd, 3J=5.7, 5.9, 3.6 Hz, 1H), 2.40 (s, 3H), 7.01-7.12 (m, 4H). 13C-NMR (CDC13, δ) 2.2, 12.1, 19.5, 20.2, 24.55, 24.6, 83.1, 125.6, 125.1, 125.9, 129.6, 140.9. IR (neat, cm-1) 2978 (m), 2931 (m), 1605 (m), 1493 (m), 1417 (s), 1318 (s), 1215 (m), 1143 (s), 859 (m), 757 (m), 732 (m), 669 (m).

With respect to the boryl cyclopropane ((E)-3h) obtained in embodiment 47, the chemical name of this compound is 2-[(E)-2-(2,4-dimethylphenyl)cyclopropyl]-4,4,5,5-tetramethyl-1,3,2-dioxaborolan. Identification data is as follows. 1H-NMR (CDC13, δ) 0.11 (ddd, 3J=6.1, 6.5, 9.5 Hz, 1H), 0.99 (ddd, 3J=5.9, 9.5 Hz, 2J=3.3 Hz, 1H), 1.10 (ddd, 3J=6.5, 7.8 Hz, 2J=3.3 Hz, 1H), 1.26 (s, 12H), 2.05 (ddd, 3J=5.9, 6.1, 3.3 Hz, 1H), 2.28 (s, 3H), 2.36 (s, 3H), 6.94 (d, J=15.2 Hz, 3H). 13C-NMR (CDC13, δ) 2.8, 12.0, 19.3, 19.9, 20.74, 24.5, 83.0, 125.7, 126.3, 130.5, 135.4, 137.8.

With respect to the allyl compound ((E)-2j) used in embodiment 49, the chemical name of this compound is (E)-3-(4-methoxyphenyl)-2-propene-1-yl methyl carbonate ester. Identification data is as follows. 1H-NMR (CDC13, δ) 3.81 (d, J=3.0 Hz, 6H), 4.77 (dd, J=0.6, 6.6 Hz, 2H), 6.17 (dt, J=6.6, 16 Hz, 1H), 6.86 (d, J=16 Hz, 1H), 6.86 (d, J=8.8 Hz, 2H), 7.34 (d, J=8.8 Hz, 2H).

With respect to the boryl cyclopropane ((E)-3j) obtained in embodiment 49, the chemical name of this compound is 2-[(E)-2-(4-methoxylphenyl)cyclopropyl]-4,4,5,5-tetramethyl-1,3,2-dioxaborolan. Identification data is as follows. 1H-NMR (CDC13, δ) 0.22 (ddd, 3J=5.6, 6.8, 10 Hz, 1H), 0.93 (ddd, 3J=5.3, 10 Hz, 2J=3.7 Hz, 1H), 1.10 (ddd, 3J=6.8, 7.8 Hz, 2J=3.7 Hz, 1H), 1.26 (s, 12H), 2.07 (ddd, 3J=5.3, 5.6, 3.7 Hz, 1H), 3.77 (s, 3H), 6.78-7.28 (m, 4H).

With respect to the allyl compound ((Z)-2j) used in embodiment 50, the chemical name of this compound is (Z)-3-(4-methoxyphenyl)-2-propene-1-yl methyl carbonate ester. Identification data is as follows. 1H-NMR (CDC13, δ) 3.81 (d, J=6.3 Hz, 6H), 4.90 (dd, J=1.4, 6.6 Hz, 2H), 5.75 (dt, J=6.6, 12 Hz, 1H), 6.64 (d, J=12 Hz, 1H), 6.90 (d, J=1.9 Hz, 2H), 7.17 (d, J=8.8 Hz, 2H). 13C-NMR (CDC13, δ) 55.4, 55.8, 114.5, 124.1, 129.2, 130.8, 133.8, 156.5, 159.8.

With respect to the boryl cyclopropane ((E)-3k) obtained in embodiment 51, the chemical name of this compound is 2-[(E)-2-(4-fluorophenyl)cyclopropyl]-4,4,5,5-tetramethyl-1,3,2-dioxaborolan. Identification data is as follows. 1H-NMR (CDC13, δ) 0.23 (ddd, 3J=5.6, 6.8, 9.7 Hz, 1H), 0.94 (ddd, 3J=5.4, 8.1 Hz, 2J=3.8 Hz, 1H), 1.13 (ddd, 3J=6.8, 8.1 Hz, 2J=3.8 Hz, 1H), 1.25 (d, J=2.7 Hz, 12H), 2.08 (dt, 1H), 6.89-7.06 (m, 4H). 13C-NMR (CDC13, δ) 4.2, 14.6, 21.0, 24.6, 83.2, 114.8, 115.1, 127.1, 127.2, 138.9, 139.0, 159.6, 162.8.

Embodiments 56 and 57

By making changes to an allyl compound and using a chiral catalyst as a catalyst, optically active boryl cyclopropane compounds were obtained according to the same procedure as Embodiment 1, and the results were collectively shown in table 8.

TABLE 8

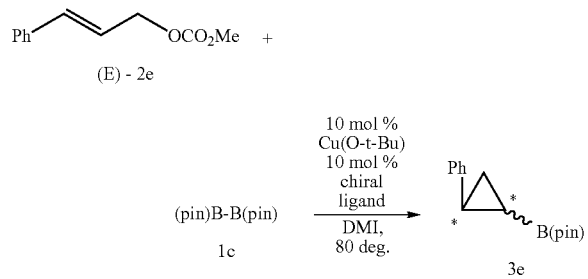

| Embodiment | Alkene | Ligand | Time (h) | Yield of 3 (%) b | Ee (S,S) (%) c | Isomer ratio trans:cis d |
|---|---|---|---|---|---|---|
| 56 | (E)-2e | (R,R)-QuinoxP | 29 | 11 | −49 | >99:1 |
| 57 | (E)-2e | (R,R)-i-Pr-Duphos | 1 | 60 | −3 | >99:1 | a condition: catalyst (10 mol %), allyl compound 2e (0.50 mmol), diboron 1a (0.50 mmol), solvent (0.25 ml).
b yield determined by NMR.
c determined by chiral GC.
d determined by GC.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A method of manufacturing an organoboron compound as shown by below-listed general formula (3) or general formula (4), the method comprising:
coupling, in the presence of a catalyst having a chiral phosphine ligand, which chiral phosphine ligand is an optically active phosphine as shown by general formula (6)

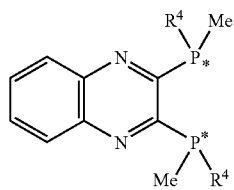

General formula (6)

where $R^4$ represents a bulky alkyl group; and * represents a chiral atom, an allyl compound as shown by below-listed general formula (1) and a diboron compound as shown by below-listed general formula (2)

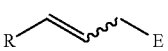

General formula (1)

where R represents a hydrogen atom, an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an alkyloxy carbonyl group, an aralkyloxy carbonyl group, or a substituted silyl group; E is an elimination group, and represents a carbonate ester, a carboxylate ester, a phosphate ester or a sulfonate ester; and the wavy line represents that either a trans- or a cis-isomer is possible;

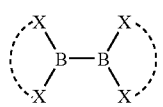

General formula (2)

where X represents identical or different atoms selected from oxygen or nitrogen; the dotted lines connecting adjacent Xs represent that other atoms are bound to Xs; and adjacent Xs may form a ring via other atoms;

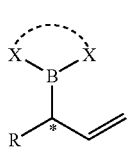

General formula (3)

where R represents an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an alkyloxy carbonyl group, an aralkyloxy carbonyl group, or a substituted silyl group; X represents identical or different atoms selected from oxygen or nitrogen; the dotted lines connecting adjacent Xs represent that other atoms are bound to Xs; and adjacent Xs may form a ring via other atoms; and * represents a chiral carbon;

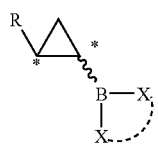

General formula (4)

where R represents an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an alkyloxy carbonyl group, an aralkyloxy carbonyl group, or a substituted silyl group; X represents identical or different atoms selected from oxygen or nitrogen; the dotted lines connecting adjacent Xs represent that other atoms are bound to Xs; and adjacent Xs may form a ring via other atoms; * represents a chiral carbon; and the wavy line represents that either a trans- or a cis-isomer is possible.

2. The method according to claim 1, wherein the allyl compound as shown by general formula (1) with R in general formula (1) being an aralkyl group or a substituted aralkyl group, is used to form an optically active allyl boron compound as shown by general formula (3).

3. The method according to claim 1, wherein the allyl compound as shown by general formula (1) with R in general formula (1) being an aryl group, a substituted aryl group or a substituted silyl group, is used to form a racemic or optically active boryl cyclopropane compound as shown by general formula (4).

4. The method according to claim 1, wherein the catalyst is a copper (I) complex.

5. The method according to claim 4, wherein a counter ion of the copper (I) complex is an alkoxide.

6. The method according to claim 4, wherein a counter ion of the copper (I) complex is a hydride.

7. A method of manufacturing an organoboron compound as shown by below-listed general formula (4), the method comprising:
coupling, in the presence of a catalyst, an allyl compound as shown by below-listed general formula (1) and a diboron compound as shown by below-listed general formula (2)

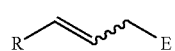

General formula (1)

where R represents a hydrogen atom, an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an alkyloxy carbonyl group, an aralkyloxy carbonyl group, or a substituted silyl group; E is an elimination group, and represents a carbonate ester, a carboxylate ester, a phosphate ester or a sulfonate ester; and the wavy line represents that either a trans- or a cis-isomer is possible;

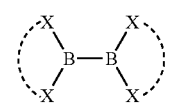

General formula (2)

where X represents identical or different atoms selected from oxygen or nitrogen; the dotted lines connecting adjacent Xs represent that other atoms are bound to Xs; and adjacent Xs may form a ring via other atoms;

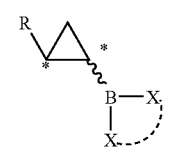

General formula (4)

where R represents an alkyl group, a substituted alkyl group, a cycloalkyl group, a substituted cycloalkyl group, an aralkyl group, a substituted aralkyl group, an aryl group, a substituted aryl group, an aliphatic heterocyclic group, a substituted aliphatic heterocyclic group, an aromatic heterocyclic group, a substituted aromatic heterocyclic group, an alkoxy group, a substituted alkoxy group, an aralkyloxy group, a substituted aralkyloxy group, an aryloxy group, a substituted aryloxy group, an alkyloxy carbonyl group, an aralkyloxy carbonyl group, or a substituted silyl group; X represents identical or different atoms selected from oxygen or nitrogen; the dotted lines connecting adjacent Xs represent that other atoms are bound to Xs; and adjacent Xs may form a ring via other atoms; * represents a chiral carbon; and the wavy line represents that either a trans- or a cis-isomer is possible.

8. The method according to claim 7, wherein the allyl compound as shown by general formula (1) with R in general formula (1) being an aryl group, a substituted aryl group or a substituted silyl group, is used to form a racemic or optically active boryl cyclopropane compound as shown by general formula (4).

9. The method according to claim 7, wherein the catalyst is a copper (I) complex.

10. The method according to claim 9, wherein a counter ion of the copper (I) complex is an alkoxide.

11. The method according to claim 9, wherein a counter ion of the copper (I) complex is a hydride.

12. The method according to claim 9, wherein the copper (I) complex has a phosphine ligand.

13. The method according to claim 12, wherein the phosphine ligand is as shown by general formula (5)

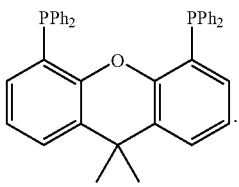

General formula (5)

14. The method according to claim 12, wherein the phosphine ligand is a chiral phosphine ligand.

15. The method according to claim 14, wherein the chiral phosphine ligand is an optically active phosphine as shown by general formula (6)

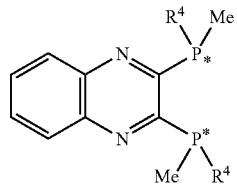

General formula (6)

where $R^4$ represents a bulky alkyl group; and * represents a chiral atom.

* * * * *